(12) United States Patent
Jin

(10) Patent No.: US 10,398,906 B2
(45) Date of Patent: Sep. 3, 2019

(54) SYSTEMS AND METHODS FOR PAIN TREATMENT USING SPINAL NERVE MAGNETIC STIMULATION

(71) Applicant: Kosivana Holdings Limited, Limassol (CY)

(72) Inventor: Yi Jin, Irvine, CA (US)

(73) Assignee: KOSIVANA HOLDINGS LIMITED, Limassol (CY)

( * ) Notice: Subject to any disclaimer, the term of this patent is extended or adjusted under 35 U.S.C. 154(b) by 418 days.

(21) Appl. No.: 15/066,754

(22) Filed: Mar. 10, 2016

(65) Prior Publication Data

US 2017/0259077 A1    Sep. 14, 2017

(51) Int. Cl.
| | | |
|---|---|---|
| *A61N 1/00* | (2006.01) | |
| *A61N 2/00* | (2006.01) | |
| *A61N 2/02* | (2006.01) | |
| *A61N 2/06* | (2006.01) | |

(52) U.S. Cl.
CPC ............. *A61N 2/008* (2013.01); *A61N 2/02* (2013.01); *A61N 2/06* (2013.01)

(58) Field of Classification Search
CPC .......... A61N 2/00; A61N 2/004; A61N 2/006; A61N 2/008
USPC ...................................................... 600/9–15
See application file for complete search history.

(56) References Cited

U.S. PATENT DOCUMENTS

| | | | |
|---|---|---|---|
| 6,042,531 A * | 3/2000 | Holcomb ................ | A61N 2/00 600/13 |
| 6,418,345 B1 | 7/2002 | Tepper et al. | |
| 6,652,443 B1 * | 11/2003 | Struppler .............. | A61N 2/006 600/9 |
| 6,776,753 B1 * | 8/2004 | Holcomb ............... | A61N 2/008 600/15 |
| 9,072,891 B1 | 7/2015 | Rao | |
| 2003/0158583 A1 | 8/2003 | Burnett et al. | |
| 2005/0228209 A1 * | 10/2005 | Schneider .......... | A61B 5/04009 600/13 |
| 2007/0260107 A1 * | 11/2007 | Mishelevich ......... | A61N 2/004 600/9 |
| 2015/0165226 A1 * | 6/2015 | Simon .................... | A61N 1/40 600/13 |
| 2015/0202454 A1 | 7/2015 | Burnett | |
| 2015/0360045 A1 * | 12/2015 | Fischell .................. | A61N 2/02 600/14 |

* cited by examiner

*Primary Examiner* — John P Lacyk
(74) *Attorney, Agent, or Firm* — Saliwanchik, Lloyd & Eisenschenk

(57) ABSTRACT

Described are methods, devices, and systems for a novel, easy-to-use treatment for pain that does not involve medication. Methods and devices herein use repetitive magnetic fields that desensitize the spinal nerve, thereby affecting transmission of pain signals from the treatment location to the brain.

21 Claims, 9 Drawing Sheets

SYSTEMS AND METHODS FOR PAIN TREATMENT USING SPINAL NERVE MAGNETIC STIMULATION

BACKGROUND OF THE INVENTION

Pain is a serious and sometimes debilitating problem. It is a symptom of many medical conditions, and can interfere with a person's quality of life and general functioning, and is the most common reason for physician consultation in most developed countries. Pain is the primary reason for more than 50% of emergency room visits, and is present in 30% of family practice visits. Pain may be either acute or chronic, persisting for minutes, such as during childbirth labor, or years, such as with rheumatoid arthritis, peripheral neuropathy, cancer, and idiopathic pain. Chronic pain is prevalent in 12-80% of the population, depending on the criteria used.

Pain is often localized to a particular region, possibly due to damage to tissue, stress, or overwork. One non-limiting example is injury to a muscle in the body, possibly due to strain or trauma. It is well known in the literature that specific locations in the body communicate pain to the brain through at least one spinal nerve. 31 pairs of spinal nerves exist in the body, with each one connecting to the spine via its nerve root. Mapping has been performed and published, which allows one to determine the spinal nerve or spinal nerves that communicate with a specific region of the body. One non-limiting example is cervical spinal nerves C5 and C6, which pass pain signals from the deltoid muscle of the shoulder to the brain.

Pain is generally managed with medications such as analgesics and anesthetics. Simple pain medications are useful in 20-70% of cases. Opioid pain relievers, such as codeine, meperidine, and oxycodone, are highly prevalent, with 207 million prescriptions written in the U.S. in 2013; however, pain medication often comes with significant side effects, which may include, but are not limited to, respiratory depression, constipation, dizziness, lightheadedness, feeling faint, drowsiness, nausea, vomiting, and addiction.

Many pain relievers are highly addictive when taken for extended periods, and the body tends to develop a tolerance to the medication, whereby a larger and larger dosage is required over time to achieve the same effect. It is apparent that a non-invasive, drug-free method for providing improved pain relief would be incredibly useful and desired.

Repetitive magnetic stimulation (rMS) uses a magnetic field generator that is placed near a target location and generates a series of magnetic field pulses roughly the strength of an MRI scan. One common use of rMS is transcranial stimulation to reduce the symptoms of a mental disorder, referred to as repetitive transcranial magnetic stimulation (rTMS).

SUMMARY

Described herein are methods and systems for novel, effective, treatment of pain. The methods and devices described herein involve no medication. The methods and devices described herein desensitize one or more spinal nerves that connect with a treatment area in the body, which may provide pain reduction.

In accordance with the subject invention, transcutaneous repetitive magnetic stimulation (rMS) at high frequency, when placed over the nerve root of the spinal nerve that connects to the location of the body requiring treatment, causes a desensitization of the spinal nerve, thereby reducing the severity of the pain in the treatment location.

In one aspect of the present invention, a method of treating pain in a person is described, comprising: (a) determining a treatment location in the body of the person that is or has been a source of pain for the person; and (b) determining a target location on or near at least one spinal nerve that connects the treatment location to the spine ipsilateral to the treatment location; and (c) administering repetitive magnetic field pulses to the target location.

The frequency or frequencies of magnetic pulses are chosen such that the spinal nerve in the target location is desensitized.

In some embodiments of at least one aspect described above, the magnetic pulse frequency is fixed at or near a target frequency. In some embodiments of at least one aspect described above, the magnetic pulse frequency hops periodically about an average target frequency. In some embodiments of at least one aspect described above, the magnetic pulse frequency hops periodically to random values within a range about an average target frequency. In some embodiments of at least one aspect described above, the magnetic pulse frequency hops periodically in a specific pattern about an average target frequency. In some embodiments of at least one aspect described above, the magnetic pulse frequency hops periodically between two values about an average target frequency.

In some embodiments of at least one aspect described above, the magnetic pulse target frequency is from about 1 Hz to about 30 Hz, or from 5 Hz to 25 Hz. In some embodiments of at least one aspect described above, the magnetic pulse target frequency is from about 30 Hz to about 100 Hz, or from 40 Hz to 75 Hz. In some embodiments of at least one aspect described above, the magnetic pulse target frequency is greater than about 100 Hz, or greater than 150 Hz.

Pulses may be part of a pulse train, with a specific overall duty cycle wherein the pulse train is active for a certain period of time, then inactive, and restarts every duty cycle period for the treatment duration. In some embodiments of at least one aspect described above, the repetitive magnetic pulses are part of a pulse train with a train duration that is about 4 seconds to about 8 seconds, or 5 second to 7 seconds, and is alternately active and inactive as part of a duty cycle with a period of about 30 seconds to about 80 seconds, or 40 seconds to 60 seconds. In some embodiments of at least one aspect described above, the pulse train duration is about 1 second to about 5 seconds, or 2 seconds to 4 seconds, and the duty cycle period is about 3 seconds to about 30 seconds, or 5 seconds to 25 seconds.

Treatment may be administered for a length of time necessary to achieve efficacy for the therapy. In some embodiments of at least one aspect described above, the treatment is administered for a treatment duration that is up to about 10 minutes, including, for example, from 1 minute to 8 minutes. In some embodiments of at least one aspect described above, the treatment is administered for a treatment duration that is from 10 minutes to about 30 minutes, or longer.

The target location is chosen to be at least one portion of the spinal nerve close to the nerve root ipsilateral to the treatment location. In some embodiments of at least one aspect described above, the target location is from about 0 inches to about 2 inches from the spine. In some embodiments of at least one aspect described above, the target location is from about 2 inches to about 4 inches or more from the spine.

The magnetic field pulse strength may be set to a value that provides effective therapy. In some embodiments of at least one aspect described above, the strength of the magnetic field pulses is from about 10 Gauss to about 4 Tesla, or from about 1000 Gauss to about 1 Tesla, or from about 5,000 Gauss to about 9,000 Gauss. In some embodiments of at least one aspect described above, the strength of the magnetic field pulses is adjusted based on the tolerance of the person. The tolerance of the person is based on the threshold above at which the magnetic pulses cause unacceptable discomfort in the target location. In some embodiments of at least one aspect described above, the method described herein may be used to treat pain caused by at least one of strenuous exercise, muscle recovery, sports injury, traumatic injury, neuromuscular injury, childbirth labor pains, gout, or peripheral neuropathy.

In addition to transmitting magnetic pulses to a target location in the spinal nerve of the person, improved pain reduction may be achieved by transmitting magnetic pulses to the treatment location directly, which causes a desensitization of the spinal nerve at the treatment location as well as the target location.

In some embodiments of at least one aspect described above, the method further comprises administration of repetitive magnetic pulses to include the treatment location in addition to the target location. In some embodiments of at least one aspect described above, repetitive magnetic pulses are administered to the treatment location and the target location concurrently. In some embodiments of at least one aspect described above, repetitive magnetic pulses are administered to the treatment location and the target location non-concurrently.

In another aspect of the present invention, a device is provided comprising:
a. a magnetic field generator; and
b. a power source configured to energize the magnetic field generator in order to generate a repetitive pulsed magnetic field outside a person, or a connector for connecting to such a source; and
c. an adjustable mount that is configured to hold the magnetic field generator in place;
wherein the magnetic field generator is configured to transmit repetitive magnetic field pulses such that the magnetic field induces an electric current in a target location on or near the spinal nerve that connects a pain treatment location to the spine.

In some embodiments of at least one aspect described above, the adjustable mount is configured to position the magnetic field generator above the target location, outside but close to the skin of the person. In some embodiments of at least one aspect described above, the target location is at a distance of about 0 inches to about 4 inches from the spine. In some embodiments of at least one aspect described above, the mount is attached to the body so that the magnetic field generator may be worn by the person. In some embodiments of at least one aspect described above, the mount is held stationary so that the person positions his/her body near the mount in order to bring the target location close to the magnetic field generator.

It is possible to incorporate the mount as part of a treatment chair, which allows the person to sit in the chair and adjust his/her body so as to place the magnetic field generator near the target area. Incorporating the mount into a chair makes positioning easier, because the person's body may naturally rest in the correct position. In some embodiments of at least one aspect described above, the mount is part of a treatment chair. The mount does not need to be in a fixed location on the chair. The target location may change based on the treatment location. In addition, the size of people varies so that the treatment location may naturally rest against a different part of the treatment chair. Therefore, it may be advantageous to allow the mount position to be adjustable. In some embodiments of at least one aspect described above, the mount position is adjustable to allow a person to move the magnetic field generator near the target location.

Instead of repositioning the magnetic field generator depending on target location and the size of the person, it may be advantageous to include multiple magnetic field generators in the treatment chair, whereby a particular magnetic field generator or magnetic field generators may be selected to transmit magnetic field pulses, depending on which magnetic field generator is closest to the target location of the person. In some embodiments of at least one aspect described above, the device further comprises a second magnetic field generator as part of the treatment chair, whereby at least one of the magnetic field generators may be selected using a switch to transmit repetitive magnetic stimulation to one or more target locations. In some embodiments of at least one aspect described above, the first magnetic field generator and the second magnetic field generator transmit repetitive magnetic stimulation to target locations concurrently. In some embodiments of at least one aspect described above, the first magnetic field generator and the second magnetic field generator transmit repetitive magnetic stimulation to target locations non-concurrently.

In addition to transmitting magnetic pulses to a target location in the spinal nerve of the person, improved pain reduction may be achieved by transmitting magnetic pulses to the treatment location directly, which causes a desensitization of the spinal nerve at the treatment location as well as the target location. In some embodiments of at least one aspect described above, the device further comprises a second magnetic field generator and mount in order to transmit repetitive magnetic field pulses to the pain treatment location directly. In some embodiments of at least one aspect described above, the first and second magnetic field generators transmit repetitive magnetic stimulation to the pain treatment location and the corresponding target location concurrently. In some embodiments of at least one aspect described above, the first and second magnetic field generators transmit repetitive magnetic stimulation to the pain treatment location and the corresponding target location non-concurrently.

In some embodiments of at least one aspect described above, the device further comprises a user interface to allow the person or a caregiver to initiate the magnetic pulses. In some embodiments of at least one aspect described above, a button is used by at least one of the persons or a caregiver to initiate the magnetic pulses. In some embodiments of at least one aspect described above, the device is used to treat pain due to childbirth labor pains. The treatment could be administered only during active labor pains, thereby reducing the overall treatment required.

BRIEF DESCRIPTION OF THE DRAWINGS

A better understanding of the features and advantages of the systems and methods provided will be obtained by reference to the following detailed description that sets forth illustrative embodiments and the accompanying drawings of which.

DETAILED DESCRIPTION

Figure 1:
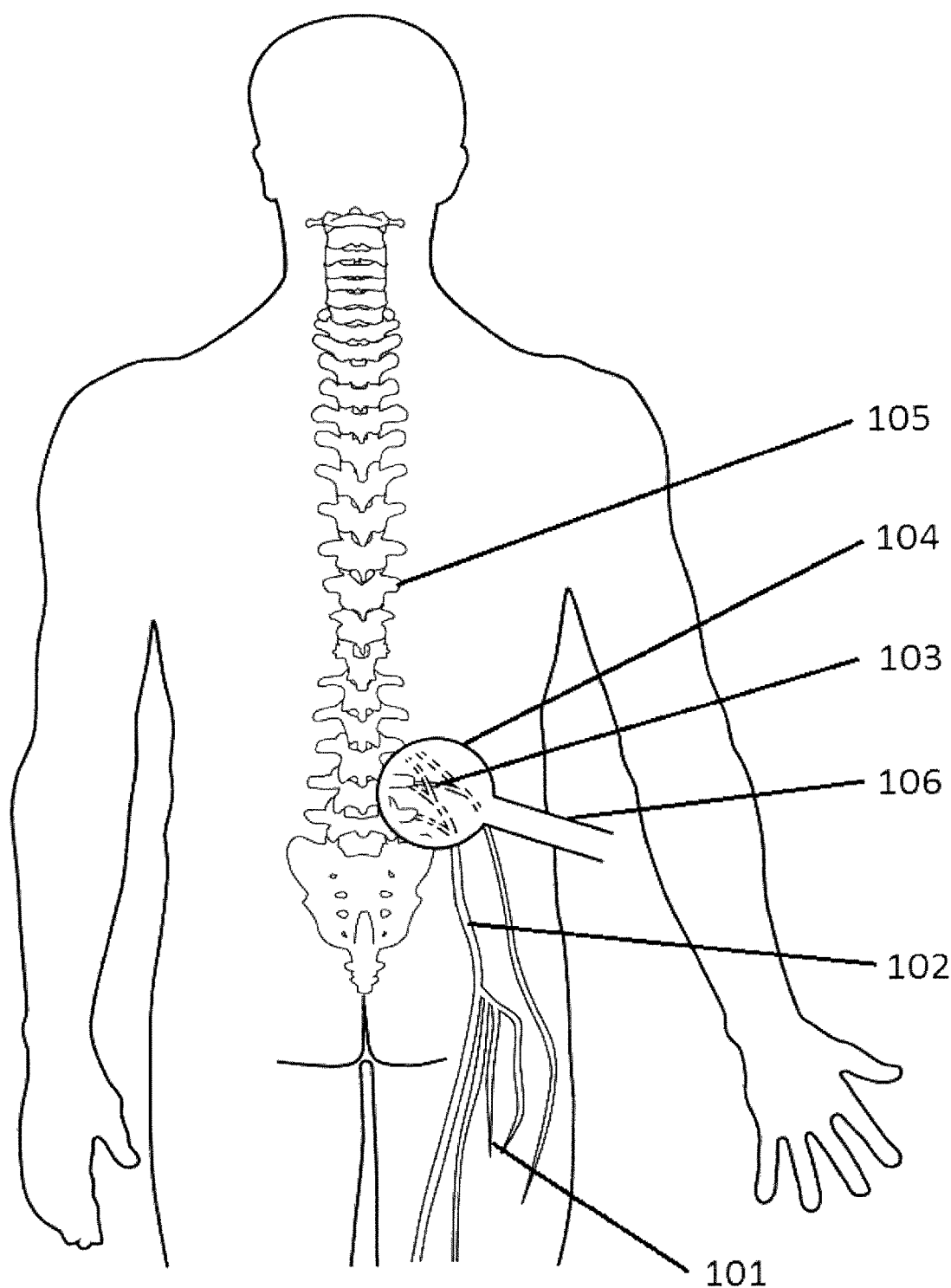
FIG. 1 shows an exemplary device in which the magnetic field generator is a coil that is placed near the root of the spinal nerve connecting the spine to a treatment location in a muscle in the thigh of a person.

While certain embodiments have been provided and described herein, it will be readily apparent to those skilled in the art that such embodiments are provided by way of example only. It should be understood that various alternatives to the embodiments described herein may be employed, and are part of the invention described herein.

Described herein are methods and systems for novel, effective, treatment of pain. In some embodiments, described are methods and systems that transmit repetitive Magnetic Stimulation (rMS) to a target location that includes a portion of at least one spinal nerve, and is located near the root of the spinal nerve where it connects to the spine. The spinal nerve connects the spine with at least one treatment location in the body of the person. When repetitive magnetic pulses are administered to a target location, the portion of the spinal nerve lying inside or near the target location becomes desensitized, which may limit the pain felt at the treatment locations to which the spinal nerve connects.

The term "treatment location," when referring to the rMS treatment, is a location which is a region of the body that is a source of pain for the person.

The term "target location," when referring to the rMS treatment, is a location near the root of a spinal nerve that connects to the treatment location. The target location is the region of the body where the rMS magnetic pulses are directed.

The term "target frequency," when referring to the rMS treatment, is the frequency of the magnetic pulses. When magnetic pulses are transmitted at a fixed frequency, the target frequency refers to this fixed value. When magnetic pulses are transmitted at a frequency that varies over time, either randomly or with a fixed pattern, the target frequency refers to the average of the magnetic pulse frequency.

The term "pulse train," when referring to the rMS treatment, is a series of magnetic pulses.

The term "duty cycle," when referring to the rMS treatment, is a periodic time interval where the pulse train is active during a portion of the time interval, where magnetic pulses are generated, and inactive during the remaining portion of the time interval, where magnetic pulses are not generated.

The term "treatment duration," when referring to the rMS treatment, is the total session time. The treatment duration is composed of a series of duty cycles.

The term "magnetic field generator," when referring to the rMS device, is the portion of the device which generates pulsed magnetic field. Examples of a magnetic field generator include a coil, a moving permanent magnet, or combination thereof. Example coils include a circular coil, a figure-8 coil, and an H-coil. Example movement of a permanent magnet include rotational motion, linear motion, and swing motion.

Described herein are methods and devices that provide treatment and involve no medication, although medication may be administered in conjunction with the treatment without necessarily altering the effects of the treatment.

When a signal is transmitted through the spinal nerve, a minimum transit time is generally required, which is about 50 milliseconds. This means that the highest frequency at which the nerve can fire is about 20 Hz (20 times per second). Magnetic pulses administered to a target location on the spinal nerve cause a voltage potential in the nerve fibers, and if the magnetic pulses have a high frequency (at least 20 Hz), then the spinal nerve becomes saturated, and desensitized to further stimulation. This desensitization means that pain signals are effectively filtered by the spinal nerve, and therefore are not felt as distinctly by the person. Typically, the person will still feel pain, but the signals will be subdued, resulting in less pain.

The target location may be anywhere along the spinal nerve; however, if magnetic pulses are delivered too close to the spine, other nerves may be affected, causing side effects. The spinal nerve may be too deep along the mid region for magnetic pulses to have the best effect. Magnetic pulses generated near the spinal nerve at the treatment location is another useful location.

In one aspect of the present invention, a method of treating pain in a person is described, comprising: (a) determining a treatment location in the body of the person that is or has been a source of pain for the person; and (b) determining a target location on or near at least one spinal nerve that connects the treatment location to the spine ipsilateral to the treatment location; and (c) administering repetitive magnetic field pulses to the target location.

The frequency or frequencies of magnetic pulses are chosen such that the spinal nerve in the target location is desensitized. In some embodiments of at least one aspect described above, the magnetic pulse frequency is fixed at or near a target frequency. In some embodiments of at least one aspect described above, the magnetic pulse frequency hops periodically about an average target frequency. In some embodiments of at least one aspect described above, the magnetic pulse frequency hops periodically to random values within a range about an average target frequency. In some embodiments of at least one aspect described above, the magnetic pulse frequency hops periodically in a specific pattern about an average target frequency. In some embodiments of at least one aspect described above, the magnetic pulse frequency hops periodically between two values about an average target frequency.

In some embodiments of at least one aspect described above, the magnetic pulse target frequency is from about 1 Hz to about 30 Hz, or from 5 Hz to 25 Hz. In some embodiments of at least one aspect described above, the magnetic pulse target frequency is from about 30 Hz to about 100 Hz, or from 40 Hz to 75 Hz. In some embodiments of at least one aspect described above, the magnetic pulse target frequency is greater than about 100 Hz, or greater than 150 Hz.

Pulses may be part of a pulse train, with a specific overall duty cycle wherein the pulse train is active for a certain period of time, then inactive, and restarts every duty cycle period for the treatment duration. In some embodiments of at least one aspect described above, the repetitive magnetic pulses are part of a pulse train with a train duration that is about 4 seconds to about 8 seconds, or 5 second to 7 seconds, and is alternately active and inactive as part of a duty cycle with a period of about 30 seconds to about 80 seconds, or 40 seconds to 60 seconds. In some embodiments of at least one aspect described above, the pulse train duration is about 1 second to about 5 seconds, or 2 seconds to 4 seconds, and the duty cycle period is about 3 seconds to about 30 seconds, or 5 seconds to 25 seconds.

Treatment may be administered for a length of time necessary to achieve efficacy for the therapy. In some embodiments of at least one aspect described above, the treatment is administered for a treatment duration that is up to about 10 minutes, including, for example, from 1 minute to 8 minutes. In some embodiments of at least one aspect described above, the treatment is administered for a treatment duration that is from 10 minutes to about 30 minutes, or longer.

The target location is chosen to be at least one portion of the spinal nerve close to the nerve root ipsilateral to the treatment location. In some embodiments of at least one aspect described above, the target location is from about 0 inches to about 2 inches from the spine. In some embodiments of at least one aspect described above, the target location is from about 2 inches to about 4 inches or more from the spine.

The magnetic field pulse strength may be set to a value that provides effective therapy. In some embodiments of at least one aspect described above, the strength of the magnetic field pulses is from about 10 Gauss to about 4 Tesla, or from about 1000 Gauss to about 1 Tesla, or from about 5,000 Gauss to about 9,000 Gauss. In some embodiments of at least one aspect described above, the strength of the magnetic field pulses is adjusted based on the tolerance of the person. The tolerance of the person is based on the threshold above which the magnetic pulses cause unacceptable discomfort in the target location. In some embodiments of at least one aspect described above, the method described herein may be used to treat pain caused by at least one of strenuous exercise, muscle recovery, sports injury, traumatic injury, neuromuscular injury, childbirth labor, gout, or peripheral neuropathy.

In addition to transmitting magnetic pulses to a target location in the spinal nerve of the person, improved pain reduction may be achieved by transmitting magnetic pulses to the treatment location directly, which causes a desensitization of the spinal nerve at the treatment location as well as the target location.

In some embodiments of at least one aspect described above, the method further comprises administration of repetitive magnetic pulses to include the treatment location in addition to the target location. In some embodiments of at least one aspect described above, repetitive magnetic pulses are administered to the treatment location and the target location concurrently. In some embodiments of at least one aspect described above, repetitive magnetic pulses are administered to the treatment location and the target location non-concurrently.

In another aspect of the present invention, a device is described comprising:
 a. a magnetic field generator; and
 b. a power source configured to energize the magnetic field generator in order to generate a repetitive pulsed magnetic field outside a person, or a connector for connecting to such a source; and
 c. an adjustable mount that is configured to hold the magnetic field generator in place;
wherein the magnetic field generator is configured to transmit repetitive magnetic field pulses such that the magnetic field induces an electric current in a target location on or near the spinal nerve that connects a pain treatment location to the spine. In some embodiments of at least one aspect described above, the target location is ipsilateral to the pain treatment location.

In some embodiments of at least one aspect described above, the adjustable mount is configured to position the magnetic field generator above the target location, outside but close to the skin of the person. In some embodiments of at least one aspect described above, the target location is at a distance of about 0 inches to about 4 inches from the spine. In some embodiments of at least one aspect described above, the mount is attached to the body so that the magnetic field generator may be worn by the person. In some embodiments of at least one aspect described above, the mount is held stationary so that the person positions his/her body near the mount in order to bring the target location close to the magnetic field generator.

It is possible to incorporate the mount as part of a treatment chair, which allows the person to sit in the chair and adjust his/her body so as to place the magnetic field generator near the target area. Incorporating the mount into a chair makes positioning easier, since the person's body may naturally rest in the correct position. In some embodiments of at least one aspect described above, the mount is part of a treatment chair. The mount does not need to be in a fixed location on the chair. The target location may change based on the treatment location. In addition, the size of people varies so that the treatment location may naturally rest against a different part of the treatment chair. Therefore, it may be advantageous to allow the mount position to be adjustable. In some embodiments of at least one aspect described above, the mount position is adjustable to allow a person to move the magnetic field generator near the target location. Instead of repositioning the magnetic field generator depending on target location and the size of the person, it may be advantageous to include multiple magnetic field generators in the treatment chair, whereby a particular magnetic field generator or magnetic field generators may be selected to transmit magnetic field pulses, depending on which magnetic field generator is closest to the target location of the person. In some embodiments of at least one aspect described above, the device further comprises a second magnetic field generator as part of the treatment chair, whereby at least one of the magnetic field generators may be selected using a switch to transmit repetitive magnetic stimulation to one or more target locations. In some embodiments of at least one aspect described above, the first magnetic field generator and the second magnetic field generator transmit repetitive magnetic stimulation to target locations concurrently. In some embodiments of at least one aspect described above, the first magnetic field generator and the second magnetic field generator transmit repetitive magnetic stimulation to target locations non-concurrently.

In addition to transmitting magnetic pulses to a target location in the spinal nerve of the person, improved pain reduction may be achieved by transmitting magnetic pulses to the treatment location directly, which causes a desensitization of the spinal nerve at the treatment location as well as the target location. In some embodiments of at least one aspect described above, the device further comprises a second magnetic field generator and mount in order to transmit repetitive magnetic field pulses to the pain treatment location directly. In some embodiments of at least one aspect described above, the first and second magnetic field generators transmit repetitive magnetic stimulation to the pain treatment location and the corresponding target location concurrently. In some embodiments of at least one aspect described above, the first and second magnetic field generators transmit repetitive magnetic stimulation to the pain treatment location and the corresponding target location non-concurrently.

In some embodiments of at least one aspect described above, the device further comprises a user interface to allow the person or a caregiver to initiate the magnetic pulses. In some embodiments of at least one aspect described above, a button is used by at least one of the person or a caregiver to initiate the magnetic pulses. In some embodiments of at least one aspect described above, the device is used to treat pain due to childbirth labor. The treatment could be administered only during active labor pains, thereby limiting the overall treatment required.

FIG. 1 shows an exemplary device in which the spinal nerve (102) connects a location on the spine (105) to a treatment location in a muscle (101) in the person's right leg. The magnetic field generator is a coil (104) in a handheld mount (106) that is placed so that the coil is above a target location (103), which includes a portion of the spinal nerve near the nerve root. Although this figure shows a handheld mount, the mount could also be affixed to a stationary bracket or other mechanism in order to prevent the coil from shifting away from the target location.

Figure 2:
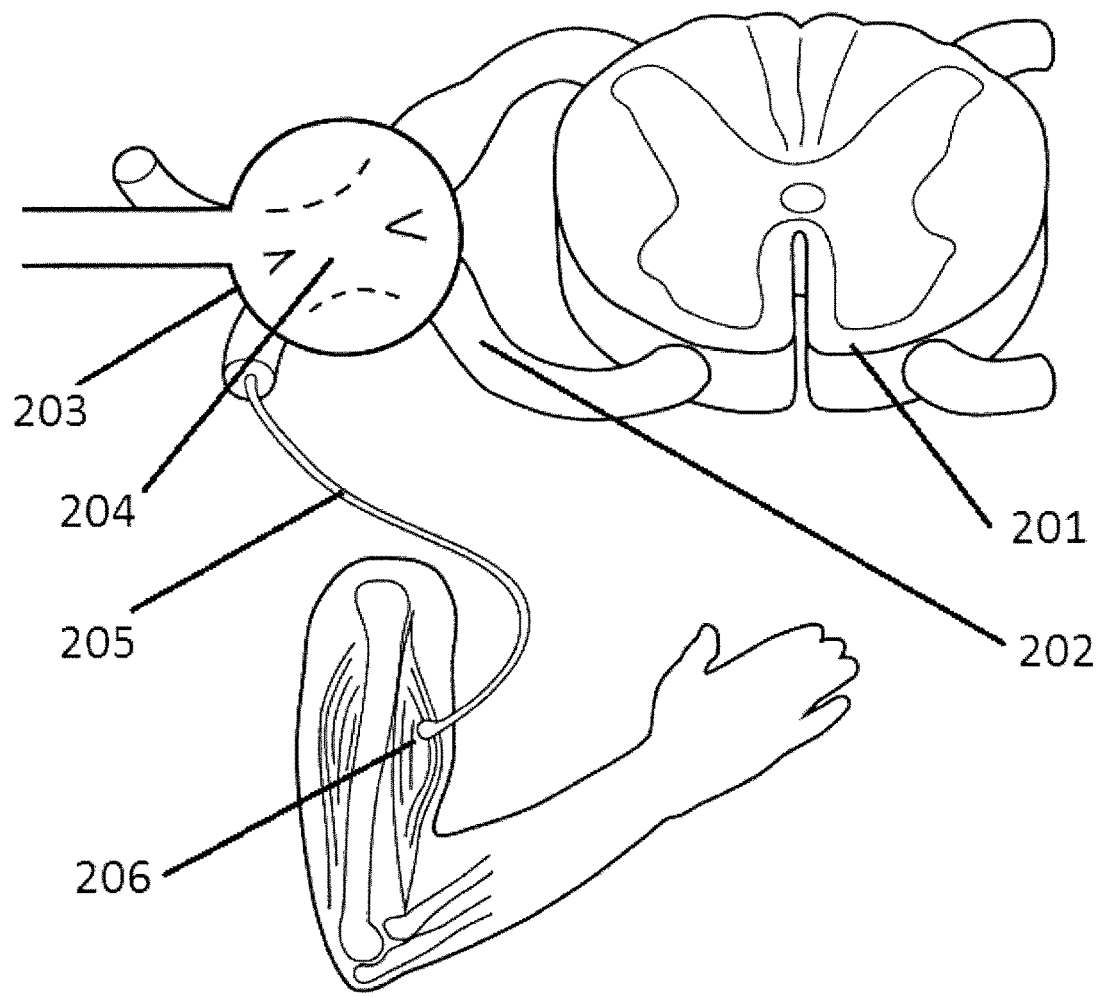
FIG. 2 shows an example target location near the nerve root of the spinal nerve connecting the spine to a treatment location in a muscle of a person.

FIG. 2 shows an example of a target location in which the spinal nerve (205) connects a location on the spine (201) to a treatment location in a muscle (206). The magnetic field generator is a coil (203) placed over the target location (204), which is located near the nerve root (202) of the spinal nerve where a connection is made to the spine.

Figure 3:
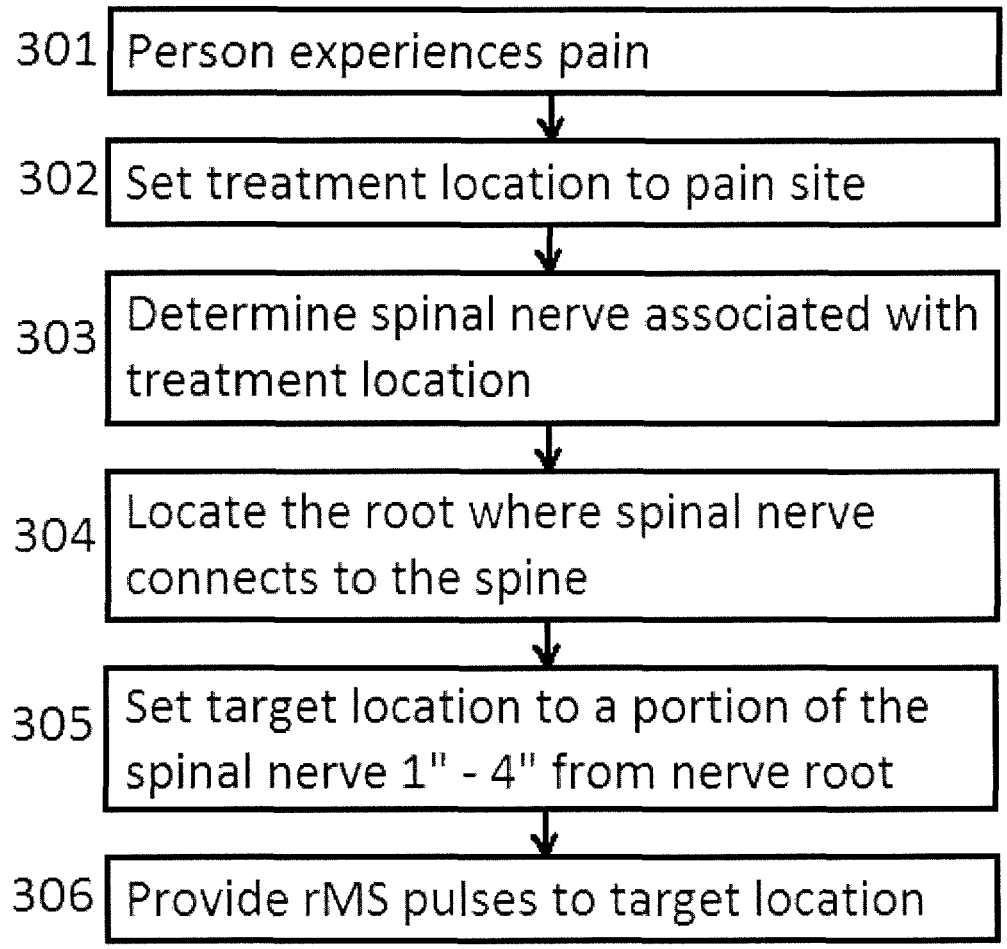
FIG. 3 shows an example method flowchart in which pain is localized and treatment is performed at a target location.

FIG. 3 shows an exemplary flowchart for one aspect of the method described herein, where a person experiences pain (301) in a portion of the body. The location where the pain occurs is registered as the treatment location (302). One or more spinal nerves connect the treatment location to the spine. These may be determined anatomically using existing references (303). Once a spinal nerve is identified as connecting the spine to the treatment location, the root of the spinal nerve is found adjacent to the spine ipsilateral to the treatment location (304). The target location is registered to a portion of the spinal nerve about 1" to about 4" from the nerve root (305). Repetitive magnetic pulses (rMS) are administered to the target location (306) in order to desensitize the spinal nerve and relieve the person's pain.

Figure 4:
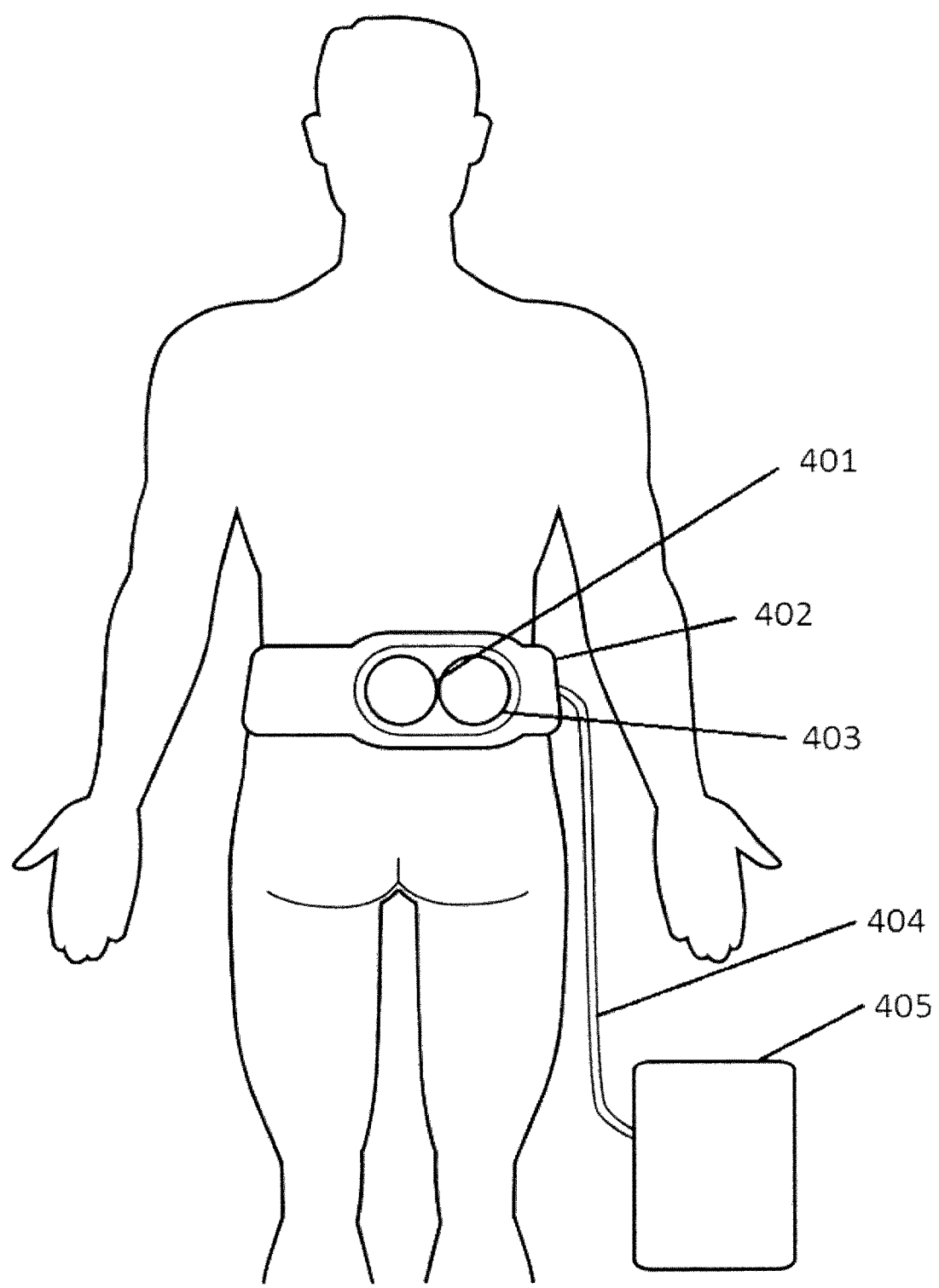
FIG. 4 shows an exemplary device in which the magnetic field generator is a coil that is held near the target location using a strap that goes around the waist or torso of the person.
Figure 8:
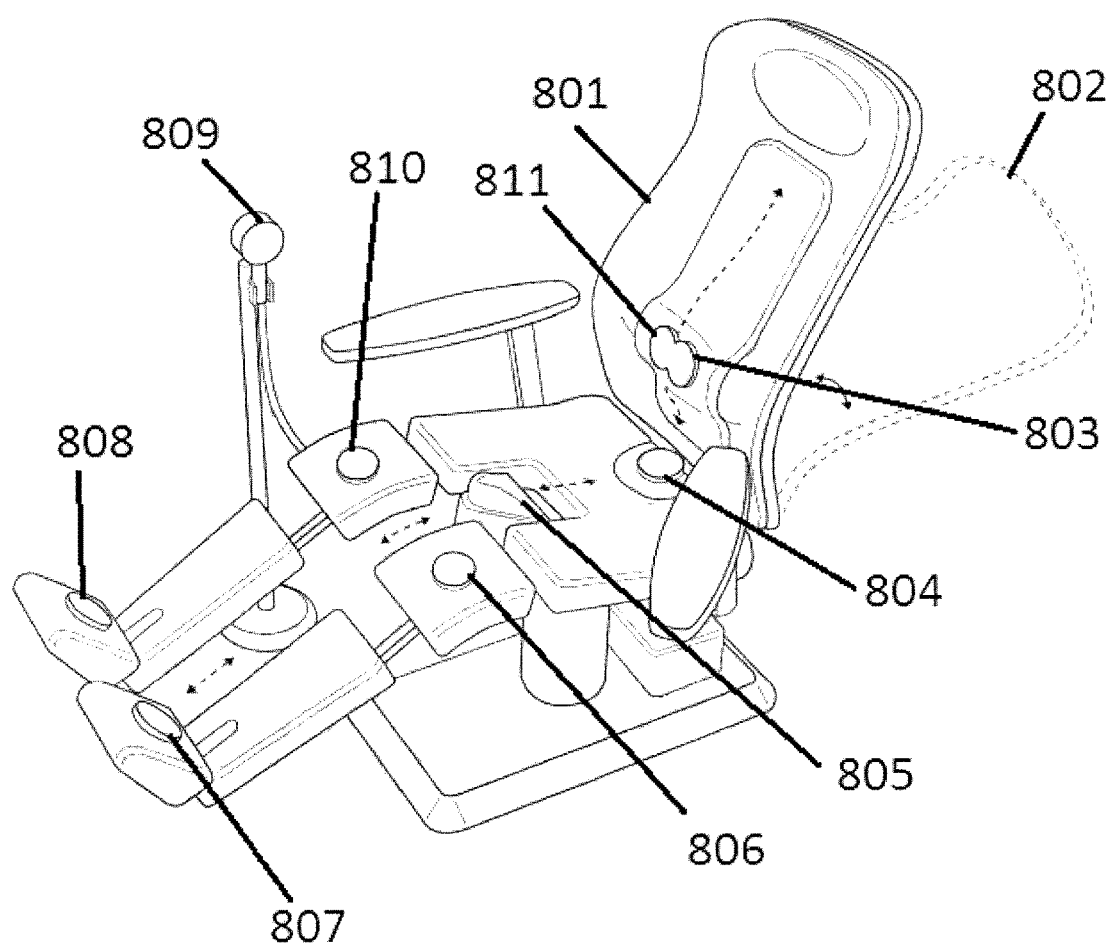
FIG. 8 shows an exemplary device in which two independent circular coils are incorporated into the back of a treatment chair, allowing at least one of the coils to be selected to target the spinal nerve on either the person's left or right. Also included are additional coils, allowing magnetic pulse stimulation to be given to treatment areas directly, for potential added benefit.

FIG. 4 shows an exemplary device in which the magnetic field generator is a figure-8 magnetic coil (403) that is contained inside a strap (402), which encircles the torso of the person. This strap is configured so that the magnetic pulses generated by the coil are directed to the target location (401). A cable (404) connects the coil with a power module (405), which controls the generation of the current pulses required to create the magnetic field pulses in the coil. The strap is shown on the person's lower waist. However, in some embodiments the strap can be raised or lowered in order to cover other target areas. Also, the coil location on the strap may be shifted so that the coil rests either a greater or lesser distance from the spine, or on the opposite side of the spine.

Figure 5:
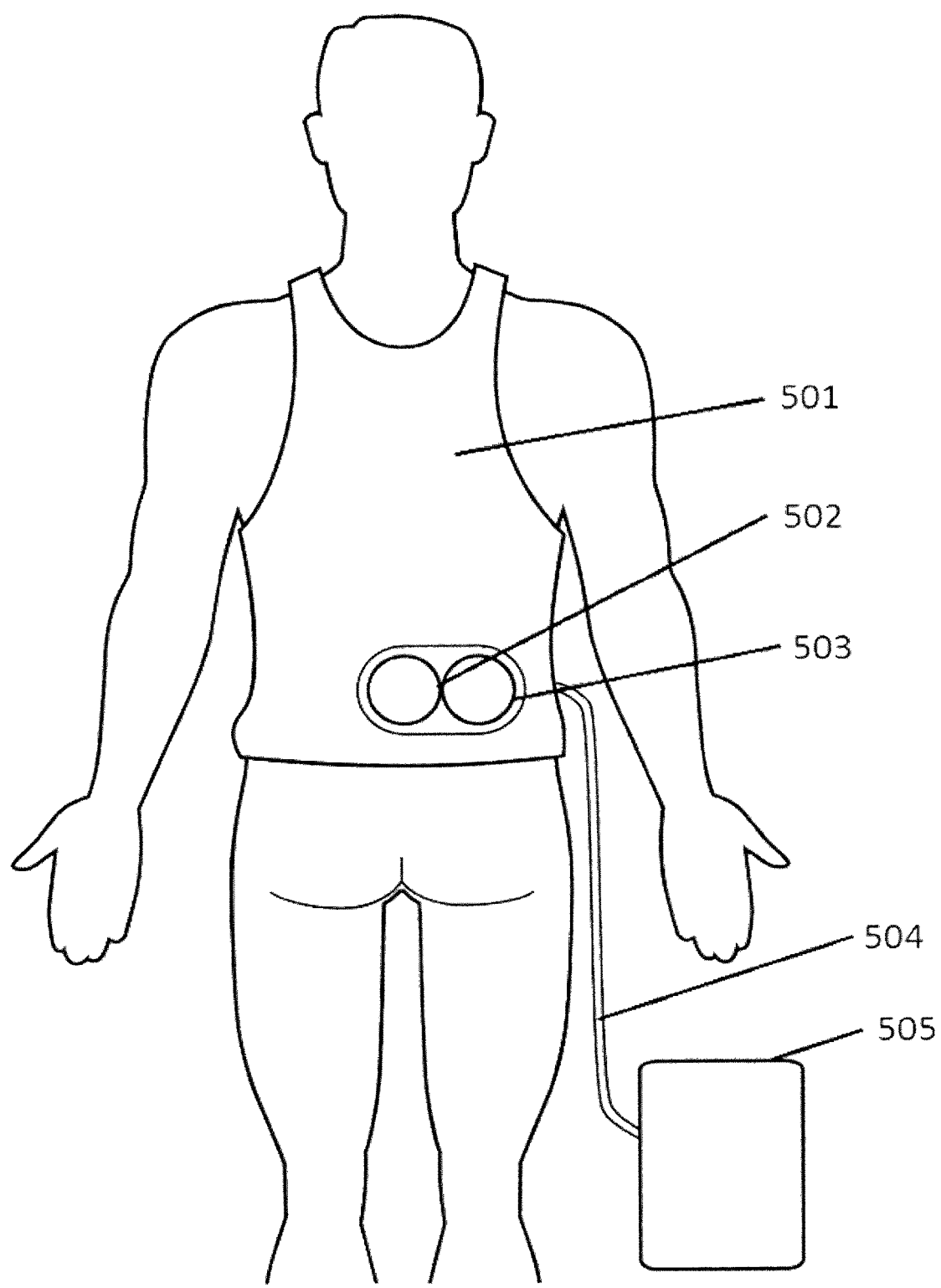
FIG. 5 shows an exemplary device in which the magnetic field generator is a coil which is contained in a vest in a location that is near the target location.

FIG. 5 shows an exemplary device in which the magnetic field generator is a figure-8 magnetic coil (503) that is contained as part of a vest (501), which is worn by the person. The vest is configured so that the magnetic pulses generated by the coil are directed to the target location (502). A cable (504) connects the coil with a power module (505), which controls the generation of the current pulses required to create the magnetic field pulses. This shows the coil over a target location situated on the person's waist. However, in some embodiments the position of the coil could be changed, either using a vest with a pocket in a different location, or by allowing the user or caregiver to adjust the coil position using Velcro or some other mechanism to secure the device in place.

Figure 6:
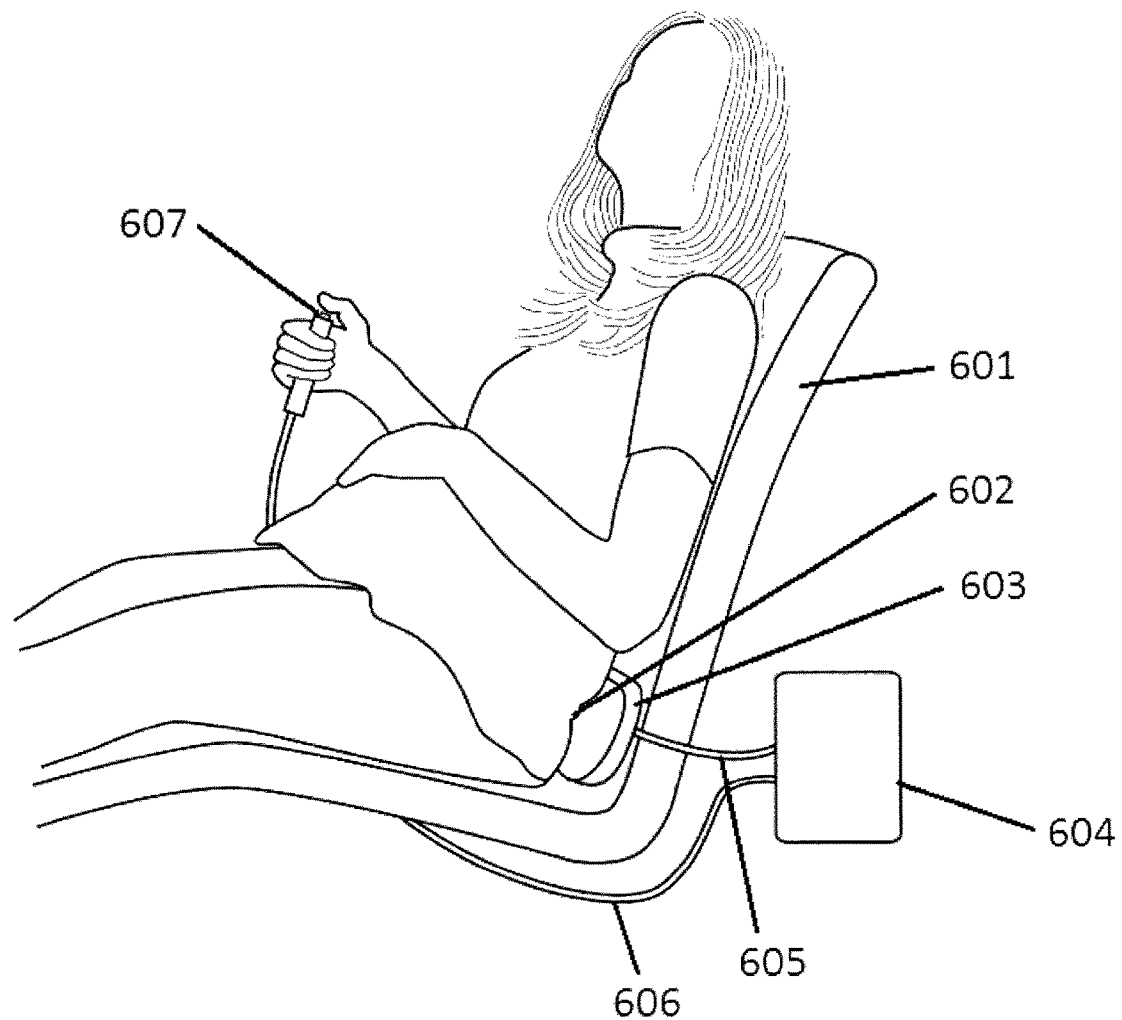
FIG. 6 shows an exemplary device in which the magnetic field generator is a coil which is used with a birthing chair and is located in a position near the target location of the person giving birth.

FIG. 6 shows an exemplary device in which the device is used in coordination with a birthing chair during childbirth. The magnetic field generator is a coil (603) that rests against or is affixed to the birthing chair (601) in a position so the magnetic pulses generated by the coil are directed towards the target location (602). A cable (605) connects the coil with a power module (604), which controls the generation of the current pulses required to create the magnetic field pulses. The patient has the ability to initiate and stop therapy by pressing a button (607), which connects to the power module through a cable (606). This configuration may perform a similar function as epidural anesthesia, in which a local anesthetic reduces the sensitivity of the spine to pain in the lower half of the body. However, the methods and devices described herein have the advantage that no medication or injection is required, reducing the risk of any possible side effects on the mother or child. In addition, the magnetic pulses are easier to control, and can be adjusted to provide optimal pain relief, while still allowing the patient to have control over the birthing process.

Figure 7:
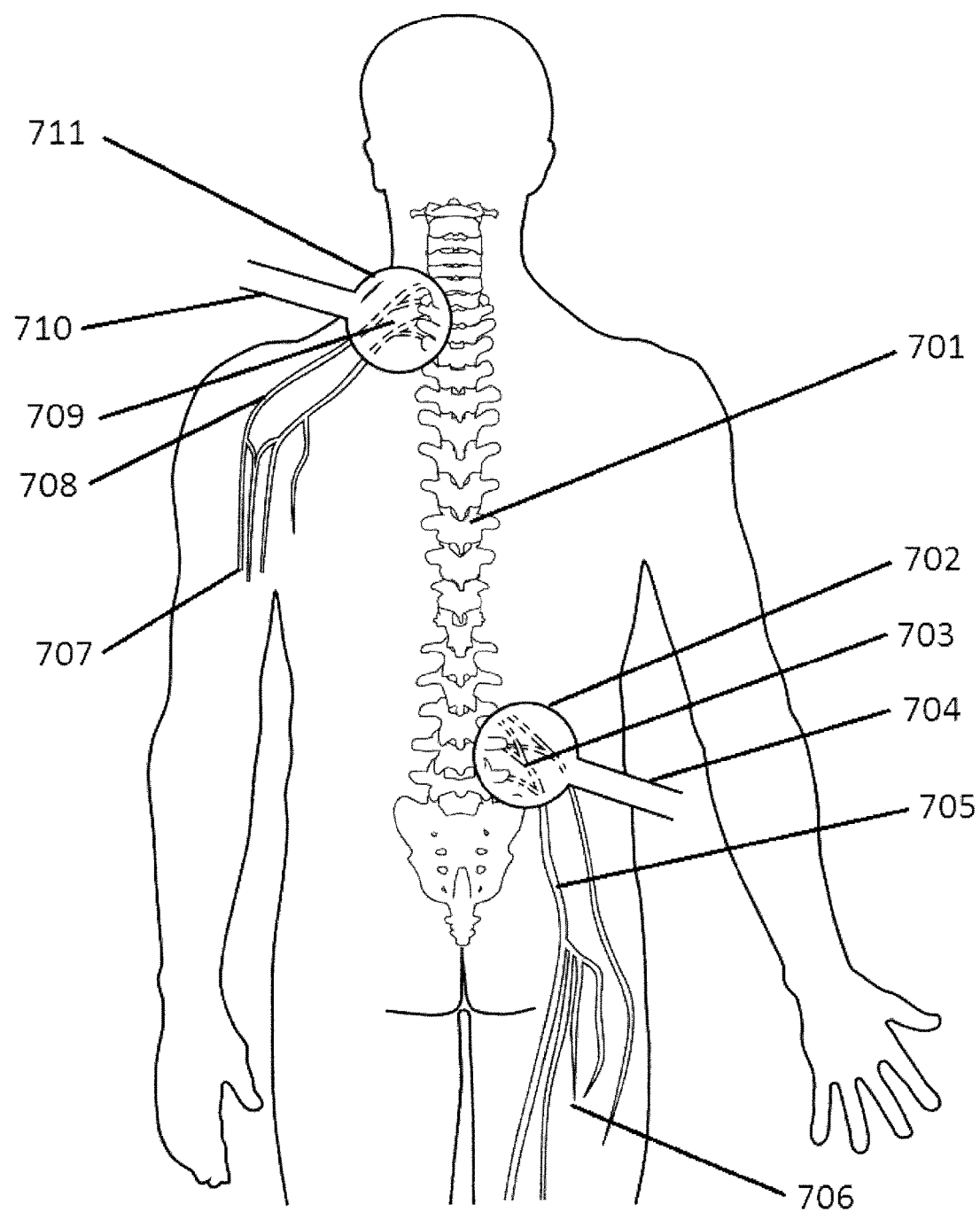
FIG. 7 shows an exemplary device in which two coils are placed near the roots of two separate spinal nerves, allowing magnetic pulses to be applied to two separate target locations in order to affect two separate treatment locations.

FIG. 7 shows an exemplary device in which 2 coils are used to administer magnetic pulses to 2 different treatment areas during the same treatment session. A treatment area in the thigh (706) is connected to the spine (701) through a spinal nerve (705). The coil (702) in a mount (704) is positioned so that magnetic field pulses are delivered to the target area (703). A second treatment area in the arm (707) is connected to a different area of the spine through a spinal nerve (708). The second coil in a mount (710) is positioned so that magnetic field pulses are delivered to the second target area (709). This figure shows two coils. However, in some embodiments more than two coils could be used to stimulate more than two target areas.

Since 31 pairs of spinal nerves exist in a person, and because magnetic pulses affect a fairly wide area, when a coil is positioned to transmit magnetic field pulses to one target area of one spinal nerve, other spinal nerves could also be affected. In some embodiments, a single spinal nerve is affected. In some embodiments, two spinal nerves are affected. In some embodiments, three spinal nerves are affected. In some embodiments, more than three spinal nerves are affected. Affecting multiple spinal nerves with a single coil allows the option of treatment of multiple target areas with a single coil.

FIG. 8 shows an exemplary device in which circular coils are incorporated into a treatment chair (801). One coil (803) is positioned to transmit magnetic field pulses to a target location to the left of the person's spine. The other coil (811) is positioned to transmit magnetic field pulses to a target location to the right of the person's spine. These coils are contained in a mount, which can be adjusted up and down along the midline of the back of the treatment chair. The back may be reclined (802) to allow for better comfort in positioning of the coils. In addition to the coils directed at target areas near the spine, the chair includes additional coils that allow magnetic pulses to be delivered to potential treatment locations on the body of the person. Coils (807) and (808) treat the soles of the feet, which may be useful in treating pain due to plantar fasciitis or gout. Coils (806) and (810) treat the knees, which may be useful in treating pain due to bursitis, osteoarthritis, or patellar tendonitis. Coil (805) treats the pelvic region, which may be useful in treating pain due to hernia. Coil (804) treats the base of the spine, which may be useful in treating lower back pain. In addition, a handheld coil (809) may be placed near another treatment location that is now accessible by existing coils.

Figure 9:
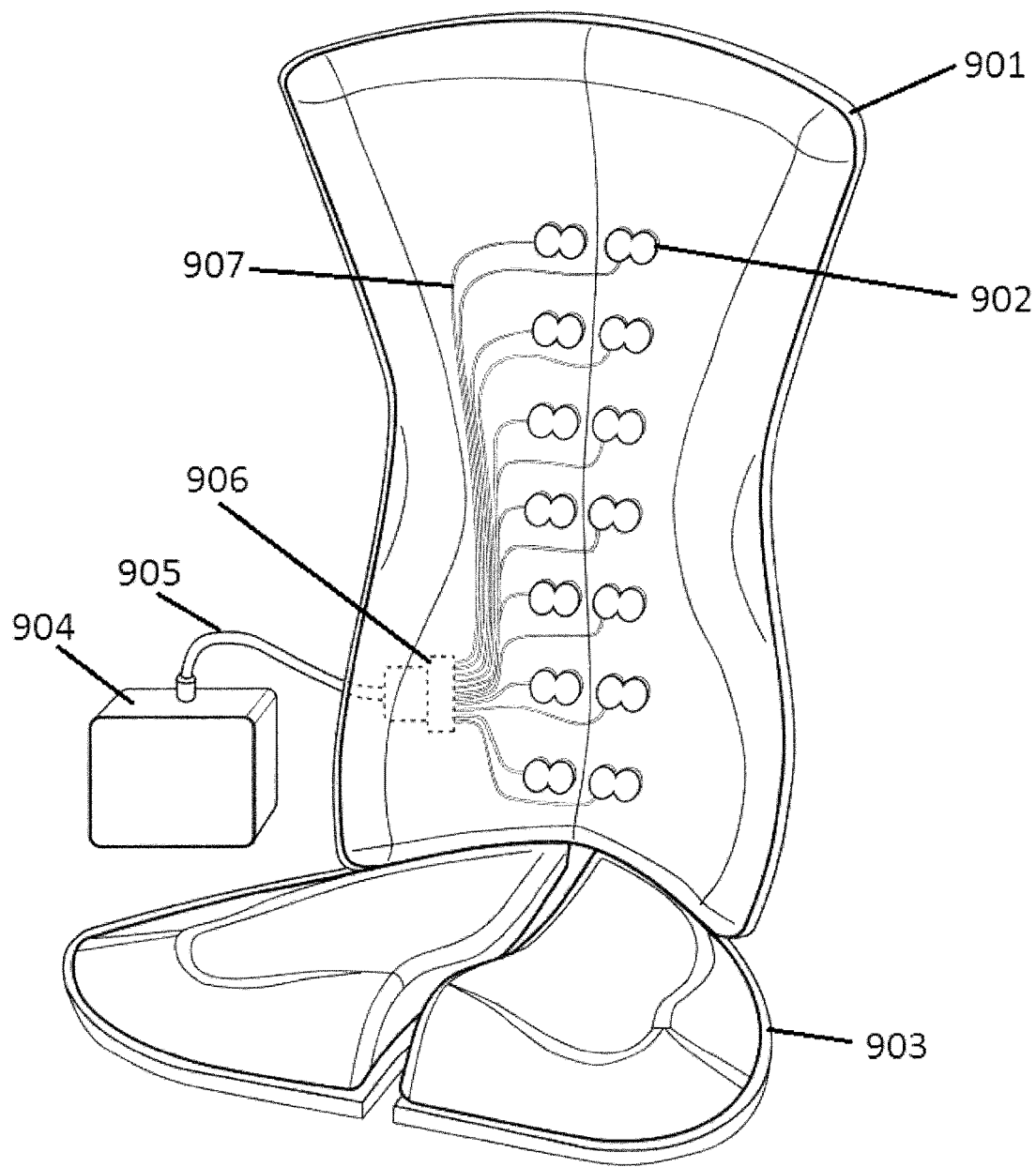
FIG. 9 shows an exemplary device in which a series of figure-8 coils are incorporated into the back of a treatment chair. Through the use of a switch, at least one of the coils may be selected to target one or more spinal nerves.

FIG. 9 shows an exemplary device in which fourteen figure-8 coils (902) are incorporated into the back of a treatment chair (901). The coils are arranged on either side of the midline of the chair. The coils are connected via cables (907) to a switch (906) that connects to the power module (904) by a cable (905). This configuration allows selective activation of one or more coils to treat one or more target areas on either side of the spine.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described.

The elements and acts of the various embodiments described can be combined to provide further embodiments. These and other changes can be made to the system in light of the above detailed description.

In general, in the following claims, the terms used should not be construed to limit the system, methods, or devices to the specific embodiments disclosed in the specification and the claims, but should be construed to include all processing systems that operate under the claims. Accordingly, the system, methods, and devices are not limited by the disclosure, but instead the scopes of the system, methods, or devices are to be determined entirely by the claims.

While certain aspects of the system, methods, or devices are presented below in certain claim forms, the inventor contemplates the various aspects of the system, methods, or devices in any number of claim forms. Accordingly, the inventors reserve the right to add additional claims after filing the application to pursue such additional claim forms for other aspects of the system, methods, or devices.

EMBODIMENTS

Specific embodiments of the invention include the following:

1. A method of treating pain in a person comprising:
   a. determining a treatment location in the body of the person that is or has been a source of pain for the person; and
   b. determining a target location on or near at least one spinal nerve that connects the treatment location to the spine ipsilateral to the treatment location; and
   c. administering repetitive magnetic field pulses to the target location.
2. The method of embodiment 1, wherein the magnetic pulse frequency is fixed at or near a target frequency.
3. The method of embodiment 1, wherein the magnetic pulse frequency hops periodically about an average target frequency.
4. The method of embodiment 3, wherein the magnetic pulse frequency hops periodically to random values within a range about an average target frequency.
5. The method of embodiment 3, wherein the magnetic pulse frequency hops periodically in a specific pattern about an average target frequency.
6. The method of embodiment 3, wherein the magnetic pulse frequency hops periodically between two values about an average target frequency.
7. The method of embodiment 2 or 3, wherein the magnetic pulse target frequency is from about 1 Hz to about 30 Hz.
8. The method of embodiment 2 or 3, wherein the magnetic pulse target frequency is from about 30 Hz to about 100 Hz.
9. The method of embodiment 2 or 3, wherein the magnetic pulse target frequency is greater than about 100 Hz.
10. The method of embodiment 2 or 3, wherein the repetitive magnetic pulses are part of a pulse train with a train duration that is about 4 seconds to about 8 seconds and is alternately active and inactive as part of a duty cycle with a period of about 30 seconds to about 80 seconds.
11. The method of embodiment 2 or 3, wherein the repetitive magnetic pulses are part of a pulse train with a train duration that is about 1 second to about 5 seconds and is alternately active and inactive as part of a duty cycle with a period of about 3 seconds to about 30 seconds.
12. The method of embodiment 1, wherein treatment is administered for a treatment duration that is about 0 minutes to about 10 minutes.
13. The method of embodiment 1, wherein treatment is administered for a treatment duration that is about 10 minutes to about 30 minutes.
14. The method of embodiment 1, wherein the target location is from about 0 inches to about 2 inches from the spine.
15. The method of embodiment 1, wherein the target location is from about 2 inches to about 4 inches from the spine.

16. The method of embodiment 1, wherein the strength of the magnetic field pulses is from about 10 Gauss to about 4 Tesla.
17. The method of embodiment 16, wherein the strength of the magnetic field pulses is adjusted based on the tolerance of the person.
18. The method of embodiment 1, wherein the pain is caused by at least one of strenuous exercise, muscle recovery, sports injury, traumatic injury, neuromuscular injury, childbirth labor, gout, or peripheral neuropathy.
19. The method of embodiment 1, further comprising administration of repetitive magnetic pulses to include the treatment location in addition to the target location.
20. The method of embodiment 19, wherein repetitive magnetic pulses are administered to the treatment location and the target location concurrently.
21. The method of embodiment 19, wherein repetitive magnetic pulses are administered to the treatment location and the target location non-concurrently.
22 A device to treat pain in a person comprising:
 a. a magnetic field generator; and
 b. a power source configured to energize the magnetic field generator in order to generate a repetitive pulsed magnetic field outside a person; and
 c. a mount that is configured to hold the magnetic field generator in place;
wherein the magnetic field generator is configured to transmit repetitive magnetic field pulses such that the magnetic field induces an electric current in a target location on or near the spinal nerve that connects a pain treatment location to the spine.
23. The device of embodiment 22, wherein the target location is at a distance of about 0 inches to about 4 inches from the spine.
24. The device of embodiment 22, wherein the mount is attached to the body so that the magnetic field generator may be worn by the person.
25. The device of embodiment 22, wherein the mount is held stationary so that the person positions his/her body near the mount in order to bring the target location close to the magnetic field generator.
26. The device of embodiment 25, wherein the mount is part of a treatment chair.
27. The device of embodiment 26, wherein the mount position is adjustable to allow a person to move the magnetic field generator near the target location.
28. The device of embodiment 26, further comprising a second magnetic field generator as part of the treatment chair, whereby at least one of the magnetic field generators may be selected using a switch to transmit repetitive magnetic stimulation to one or more target locations.
29. The device of embodiment 28, wherein the first magnetic field generator and the second magnetic field generator transmit repetitive magnetic stimulation to target locations concurrently.
30. The device of embodiment 28, wherein the first magnetic field generator and the second magnetic field generator transmit repetitive magnetic stimulation to target locations non-concurrently.
31. The device of embodiment 26, further comprising a second magnetic field generator and mount in order to transmit repetitive magnetic field pulses to the pain treatment location directly.
32. The device of embodiment 31, wherein the first and second magnetic field generators transmit repetitive magnetic stimulation to the pain treatment location and the corresponding target location concurrently.
33. The device of embodiment 31, wherein the first and second magnetic field generators transmit repetitive magnetic stimulation to the pain treatment location and the corresponding target location non-concurrently.
34. The device of embodiment 22, further comprising a user interface to allow the person or a caregiver to initiate the magnetic pulses.
35. The device of embodiment 34, wherein the user interface is a button.
36. The device of embodiment 34, wherein the device is used to treat pain due to childbirth labor.

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The invention is described in greater detail by the following non-limiting examples.

Example 1

A 69-year-old male had suffered from lower back pain on his right side for 30 years. The patient's lumbar movement was significantly affected, causing him to bend forward approximately 15 degrees. The L3-L5 spinal nerves were identified as connecting the spine to the treatment location. The target location was selected to be one inch from the spine ipsilateral to the treatment location.

Repetitive magnetic stimulation (rMS) was administered with 8,000 Gauss pulse intensity, 50 Hz pulse frequency, with a pulse train duration of 4.0 seconds and duty cycle period 10.0 seconds. Treatment duration was two minutes.

The patient reported a 50% reduction in pain immediately following treatment. Also, he was able to walk upright without bending at the waist.

Example 2

A 53-year-old male had a right side rotator cuff injury for 1.5 years, causing severe shoulder pain. The patient's motion was limited to 30 degrees in abduction, and 20 degrees in flexion. The C5-T1 spinal nerves were identified as connecting the spine to the treatment location. The target location was selected to be one inch from the spine ipsilateral to the treatment location.

rMS was administered with 6,500 Gauss intensity, and a random hopping pulse frequency in the range of 70 Hz to 100 Hz. The pulse train duration was 3.0 seconds and duty cycle period was 6.0 seconds. Treatment duration was four minutes.

The patient reported immediate symptom reduction following treatment. Motion improved by 200%. The patient was treated daily, and reached full remission after 3 weeks of treatment.

Example 3

A 36-year-old male military veteran had severe phantom pain in the right foot for 5 years after an Incendiary Explosive Device (IED) injury and amputation above the knee. The L3-S1 spinal nerves were identified as connecting the spine to the treatment location. In this case, since the foot did not exist, the treatment location was selected as where the foot would have been. The target location was selected as one inch from the spine ipsilateral to the treatment location.

rMS was administered with 8,000 Gauss intensity, 71.4 Hz pulse frequency, with a 3 second pulse train and duty cycle period of 6 seconds. Treatment duration was 5 minutes at each location. The patient was treated daily for 4 weeks.

Symptoms disappeared completely.

Example 4

A 58-year-old female patient had pain in multiple locations across her body, due to a work related injury, and had not been employed for 18 years. To manage the pain, she ingested an equivalent dose of 700 mg of morphine per day.

Treatment locations were chosen as multiple locations on the body, with C2-T1 and L3-S1 spinal nerves identified as connecting the spine to the treatment location. The target location was selected as one inch from the spine ipsilateral to the treatment location for each spinal nerve. rMS was administered with 7,200 Gauss intensity, 100 Hz pulse frequency, with a 3 second pulse train and duty cycle period of 6 seconds. Treatment duration was 4 minutes at each location.

Following a 2-month daily treatment regimen, the patient reported that her pain severity was reduced from 8 to 2 on a 10-point scale. She reduced her pain medication to 20% of her previous prescription. She also resumed her employment.

Example 5

A 51-year-old male veteran had anxiety and a history of multiple traumatic brain and bodily injuries sustained during combat operations. He presented with an active gout flare-up, evinced in general swelling in his right ankle and foot in addition to a general throbbing moderate pain in his toe and knee.

Treatment location was chosen to be the patient's knee and toe, with L3 spinal nerves identified, with additional treatment site magnetic pulses delivered at the peroneal nerve at the ankle as well as both medial and lateral plantar nerves on his right sole.

rMS was administered with 5,000 Gauss intensity. 74 Hz pulse frequency, 221 pulses per train with a duty cycle period of 4 seconds. Treatment duration was 4 minutes at each location. The patient was treated for two days.

A greater than 70% reduction in swelling was noted by day 2 of therapy. The patient reported significant reduction in pain immediately following the initial stimulation, in addition to improvement in mobility. The patient reported that he had no pain following the first day of therapy.

What is claimed is:

1. A method of treating pain in a person comprising:
   a) determining a treatment location in the body of the person that is or has been a source of pain for the person;
   b) determining a target location that is on or near at least one spinal nerve, is a distance of 0.5 inches to about 4.0 inches from the spine of the person, and that connects the treatment location to the spine ipsilateral to the treatment location; and
   c) administering repetitive magnetic field pulses to the target location.

2. The method of claim 1, wherein a magnetic pulse target frequency of the magnetic pulses is chosen from a predetermined range such that administrating the repetitive magnetic pulses at the target frequency desensitizes the target location.

3. The method of claim 1, wherein the target location is subjected to the repetitive magnetic field pulses at a plurality of frequencies that shift within a predetermined range during a single treatment session.

4. The method of claim 3, wherein the target location is subjected to the repetitive magnetic field pulses at a plurality of frequencies that are each above an average target frequency during a single treatment session.

5. The method of claim 3, wherein the target location is subjected to the repetitive magnetic field pulses at a plurality of frequencies that shift to follow a specific pattern within a predetermined range during a single treatment session.

6. The method of claim 3, wherein the target location is subjected to the repetitive magnetic field pulses at a plurality of frequencies that shift between two values within a predetermined range during a single treatment session.

7. The method of claim 2 or 3, wherein the predetermined range of the magnetic pulse target frequency is from about 1 Hz to about 30 Hz.

8. The method of claim 2 or 3, wherein the predetermined range the magnetic pulse target frequency is from about 30 Hz to about 100 Hz.

9. The method of claim 2 or 3, wherein the predetermined range of the magnetic pulse target frequency is greater than about 100 Hz.

10. The method of claim 2 or 3, wherein the repetitive magnetic pulses are part of a pulse train with a train duration that is about 4 seconds to about 8 seconds and is alternately active and inactive as part of a duty cycle with a period of about 30 seconds to about 80 seconds.

11. The method of claim 2 or 3, wherein the repetitive magnetic pulses are part of a pulse train with a train duration that is about 1 second to about 5 seconds and is alternately active and inactive as part of a duty cycle with a period of about 3 seconds to about 30 seconds.

12. The method of claim 1, wherein treatment is administered for a treatment duration that is about 0 minutes to about 10 minutes.

13. The method of claim 1, wherein treatment is administered for a treatment duration that is about 10 minutes to about 30 minutes.

14. The method of claim 1, wherein the target location is from 0.5 inches to about 2 inches from the spine.

15. The method of claim 1, wherein the target location is from about 2 inches to about 4 inches from the spine.

16. The method of claim 1, wherein the strength of the magnetic field pulses is from about 10 Gauss to about 4 Tesla.

17. The method of claim 16, wherein the strength of the magnetic field pulses is adjusted based on the tolerance of the person.

18. The method of claim 1, wherein the pain is caused by at least one of strenuous exercise, muscle recovery, sports injury, traumatic injury, neuromuscular injury, childbirth labor, gout, and peripheral neuropathy.

19. The method of claim 1, further comprising administration of repetitive magnetic pulses to include the treatment location in addition to the target location.

20. The method of claim 19, wherein repetitive magnetic pulses are administered to the treatment location and the target location concurrently.

21. The method of claim 19, wherein repetitive magnetic pulses are administered to the treatment location and the target location non-concurrently.

* * * * *